(12) United States Patent
Magnus et al.

(10) Patent No.: US 6,326,374 B1
(45) Date of Patent: Dec. 4, 2001

(54) COMPOSITIONS COMPRISING GABA ANALOGS AND CAFFEINE

(75) Inventors: Leslie Magnus, Livingston; Catherine A. Segal, Chester, both of NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/743,371

(22) PCT Filed: Jun. 18, 1999

(86) PCT No.: PCT/US99/13670

§ 371 Date: Jan. 9, 2001

§ 102(e) Date: Jan. 8, 2001

(87) PCT Pub. No.: WO00/02562

PCT Pub. Date: Jan. 20, 2000

Related U.S. Application Data

(60) Provisional application No. 60/092,131, filed on Jul. 9, 1998.

(51) Int. Cl.[7] .................................................. A61K 31/52
(52) U.S. Cl. .............................................................. 514/264
(58) Field of Search ................................................ 514/264

(56) References Cited

U.S. PATENT DOCUMENTS

| 4,656,177 | 4/1987 | Sunshine et al. | 514/264 |
| 5,248,678 | 9/1993 | Costa et al. | 514/220 |
| 5,443,838 | 8/1995 | Koenig, Jr. | 424/439 |

FOREIGN PATENT DOCUMENTS

| 9507079 | 3/1995 | (WO) |
| 9733858 | 9/1997 | (WO) |
| 9807447 | 2/1998 | (WO) |
| 9817627 | 4/1998 | (WO) |
| 9912537 | 3/1999 | (WO) |

OTHER PUBLICATIONS

Rosenberg et al., "The Effect of Gabapentin on Neuropathic Pain", *The Clinical Journal of Pain*, vol. 13, No. 3, 1997, pp 251–255.

PCT International Search Report, PCT/US99/13670.

*Primary Examiner*—James H. Reamer
(74) *Attorney, Agent, or Firm*—Charles W. Ashbrook

(57) ABSTRACT

Compositions that comprise a GABA analog, such as gabapentin or pregabalin in combination with caffeine are disclosed. The compositions are used to treat pain in mammals.

42 Claims, No Drawings

COMPOSITIONS COMPRISING GABA ANALOGS AND CAFFEINE

This appl. is a 371 of PCT/US99/13670, filed Jun. 18, 1999, which Claims benefit of No. 60/092,131, filed Jul. 9, 1998.

BACKGROUND OF THE INVENTION

1. Field of the Invention

The present invention relates to compositions comprising analogs of glutamic acid and gamma-aminobutyric acid (GABA) in combination with a central nervous system stimulant (CNS). The present invention also relates to a method of using these compositions for treating pain.

2. Description of Related Art

GABA analogs are known agents useful in antiseizure therapy for central nervous system disorders such as epilepsy, Huntington's chorea, cerebral ischemia, Parkinson's disease, tardive dyskinesia, and spasticity. It has also been suggested that the compounds can be used as antidepressants, anxiolytics, and antipsychotics. See WO 92/09560 (U.S. Ser. No. 618,692 filed Nov. 27, 1990) and WP 93/23383 (U.S. Ser. No. 886,080 filed May 20, 1992).

WO 97/33858 teaches that compounds related to gabapentin are useful or treating epilespy, faintness attacks, hypokinesia, cranial disorders, neurodegenerative disorders, depression, anxiety, panic, pain, and neuropathological disorders. WO 97/33858 does not specify what forms of pain are treated.

Additionally, GABA analogs are known for treatment of neuropathic pain. For example, see Rosner H; Rubin L; Kestenbaum A., Gabapentin adjunctive therapy in neuropathic pain states. Clin J Pain, March, 1996 12:1, 56–8; Segal A Z; Rordorf G., Gabapentin as a novel treatment for postherpetic neuralgia. Neurology, April, 1996 46:4, 1175–6; Wetzel C H; Connelly J F., Use of gabapentin in pain management. Ann Pharmacother, September, 1997 31:9, 1082–3; Zapp J J., Postpoliomyelitis pain treated with gabapentin [letter]. Am Fam Physician, June 1996 53:8, 2442, 2445; Cheville A, et al., Neuropathic pain in radiation myelopathy:a case report. Program book, American Pain Society (14th Annual Scientific Meeting). Abstract #95823, p. A-115; Sist T; Filadora V; Miner M; Lema M., Gabapentin for idiopathic trigeminal neuralgia: report of two cases. Neurology, May, 1997 48:5, 1467; Waldman S D, Tutorial 28: Evaluation and Treatment of Trigerninal Neuralgia. Pain Digest (1997) 7:21–24; Mellick L B; Mellick G A., Successful treatment of reflex sympathetic dystrophy with gabapentin [letter]. Am J Emerg Med, January, 1995 13:1, 96; Mellick G A; Seng M I., The use of gabapentin in the treatment of reflex sympathetic dystrophy and a phobic disorder. Am J Pain Manage 1995; 5:7–9; Mellick G A; Mellicy L B; Mellick L B., Gabapentin in the management of reflex sympathetic dystrophy [letter]. J Pain Symptom Manage, May, 1995 10:4, 265–6; Mellick G A; Mellick L B., Reflex sympathetic dystrophy treated with gabapentin. Arch Phys Med Rehabil, January, 1997 78:1, 98–105 and Mackin G A., Medical and pharmacologic management of upper extremity neuropathic pain syndromes. J Hand Ther, April–June, 1997 10:2, 96–109.

Caffeine, or 3,7-dihydro-1,3,7-trimethyl-1H-purine-2,6-dione, has the structural formula:

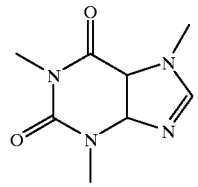

Caffeine is a central nervous system stimulant that has been used, either alone or in coinbination with other drugs, in the treatment of headaches. Compositions containing one or more of the analgesics aspirin, acetaminophen and phenacetin in combination with varying amounts of caffeine have been marketed in the past. In several cases, such non-narcotic analgesic/caffeine combination products have further included one of the narcotic analgesics codeine, propoxyphene or oxycodone. Examples of these combinations include the products known commercially as Excedrin® SK-65® Compound, Darvon® Compound, Anacin®, A.P.C., and A.P.C. with Codeine, Tabloid® Brand.

Caffeine use in the treatment of headache has a long history. The FDA Advisory Panel, in its review of caffeine [Federal Register, 1977, 42(131): 35482–35485] argued that the known biochemical effect of caffeine on small blood vessels provides a plausible explanation for its effectiveness in treating headache associated with cerebral blood vessels. Sechzer [Curr. Therapy Research, 1979, 26(4)] found that intravenous administration of caffeine sodium benzoate rapidly provided relief in the majority of patients experiencing headache resulting from dural puncture or spinal anesthesia. The author, referring to the literature on the mechanism of action of caffeine on cerebral blood flow and on cerebral vascular tone, argues from the opposite perspective of the Panel that the analgesic relief obtained implies that an intracranial vascular component is the primary factory in such headaches.

Changes in mood and over all sense of "well being" after administration of caffeine have been widely reported in the literature. Beginning in the early part of this century, Hollingsworth (Arch. Psychol., 1912, 22: 1) reported beneficial motor and mental effects from 65 to 130 mg of caffeine, and tremor, poor motor performance, and insomnia caused by 390 mg of caffeine. Many studies over the past 70 years have confirmed these findings. Review articles on the xanthines [Ritchie, J. M., "Central nervous system stimulants. 2. The xanthines," Goodman, L. S. & Gilman, A. (Eds.) The pharmacological basis of therapeutics, 4th Ed., New York: Macmillian Co., 1970; Stephenson, P. E., "Physiologic and psychotropic effects of caffeine on man," J. Amer. Diet. Assoc., 1977, 71(3): 240–247] report that doses of 50 to 200 mg of caffeine result in increased alertness, decreased drowsiness, and lessened fatigue. Doses in the range of 200 to 500 mg may produce headaches, tremor, nervousness and irritability.

After extensively reviewing the relevant literature, the FDA Advisory Panel in 1977 concluded that caffeine when used as an analgesic adjuvant was safe, but that there was insufficient data to demonstrate that caffeine contributes anything to the action of the analgesic [Federal Register, 1977, 42(131): 35482–35485]. The Panel stated: Unfortunately, the information and data submitted, fail to demonstrate conclusively that caffeine in combination is effective as an analgesic, antipyretic and/or anti-rheumatic ingredient. The Panel finds there is little evidence to show that this ingredient even contributes to these pharmacological effects in the clinical situation. This remains the official position on the question up to the present time. Consequently, many of the analgesic/caffeine combination products previously available are no longer on the market.

U.S. Pat. No. 4,656,177 discloses combinations of non-narcotic analgesics/nonsteroidal anti-inflammatory drugs and/or narcotic analgesics and caffeine. The compositions elicit a more potent and more rapid analgesic response than if the pain reliever is given alone.

U.S. Pat. No. 5,248,678 teaches a method of increasing the arousal an alertness of comatose patients or nea-comatose patients comprising administering to the patients effective amouts of an adenosine receptor antagonist, such as caffeine, and a GABA agonist, such as gabapentin.

SUMMARY OF THE INVENTION

The present inventors have discovered that a new class of pain relievers, not chemically related to aspirin, phenacetin, ibuprofen, other NSAIDS or narcotic analgesics can provide improved efficacy when combined with caffeine or other central nervous system stimulants. This invention provides a composition for treating pain including a combination of an effective amount of a GABA analog and caffeine. The GABA analog is a cyclic amino acid compound of Formula I

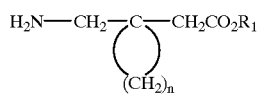

wherein $R_1$ is hydrogen or lower alkyl and n is an integer of from 4 to 6, and the pharmaceutically acceptable salts thereof. An especially preferred embodiment utilizes a compound of Formula I where $R_1$ is hydrogen and n is 4. This compound is 1-(aminomethyl)-cyclohexane acetic acid, known generically as gabapentin.

In another embodiment, the invention is directed to a composition for treating pain comprising a compound of Formula II.

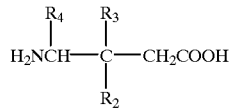

wherein $R_2$ is a straight or branched alkyl of from 1 to 6 carbon atoms, phenyl, or cycloalkyl having from 3 to 6 carbon atoms; $R_3$ is hydrogen or methyl; and $R_4$ is hydrogen, methyl, or carboxyl; or an individual enantiomeric isomer thereof; or a pharmaceutically acceptable salt thereof, in unit dosage form, to a mammal in need of said treatment; in combination with caffeine.

Preferred compounds of Formula II are those wherein $R_4$ and $R_3$ are hydrogen, and $R_2$ is $-(CH_2)_{0-2}-iC_4H_9$ as an (R), (S), or (R,S) isomer.

The more preferred compounds of Formula II are (S)-3-(aminomethyl)-5-methylhexanoic acid and 3-aminomethyl-5-methyl-hexanoic acid, now known generically as pregabalin.

The present invention also includes a method of treating pain comprising administering effective amounts of the compositions described above.

DETAILED DESCRIPTION OF THE PREFERRED EMBODIMENTS

The compositions of this invention utilize any GABA analog. A GABA analog is any compound derived from or based upon gamma-aminobutyric acid. The compounds are readily available, either commercially, or by synthetic methodology well-known to those skilled in the art of organic chemistry. The preferred GABA analogs to be utilized in the method of this invention are cyclic amino acids of Formula I. These are described in U.S. Pat. No. 4,024,175, which is incorporated herein by reference. Another preferred method utilizes the GABA analogs of Formula II, and these are described in U.S. Pat. No. 5,563,175, which is incorporated herein by reference.

All that is required to practice the method of this invention is to administer the combination of a GABA analog and caffeine in an amount that is effective to treat a mammal, especially humans, suffering from pain. The amount of GABA analog in the composition will generally be from about 1 to about 300 mg per kg of subject body weight. Typical doses will be from about 10 to about 5000 mg per day for an adult subject of normal weight. It is expected that common doses that might be administered could be from 100 mg three times a day up to 600 mg four times a day. Commercially available capsules of 100 mg, 300 mg, and 400 mg of gabapentin can be administered. Alternate forms include liquids and film-coated tablets.

If a compound of Formula II, such as pregabalin is used, the dosage level is one sixth that of gabapentin. The dosage range for pregabalin is from about 0.15 mg to about 50 mg per kg per day of subject body weight. Typical dosages for pregabalin will be from about 1.6 mg to about 840 mg per day with individual dosages ranging from abut 0.15 mg to about 65 mg per dose.

The GABA analogs of the present invention may form pharmaceutically acceptable salts with both organic and inorganic acids or bases. For example, the acid addition salts of the basic compounds are prepared either by dissolving the free base in aqueous or aqueous alcohol solution or other suitable solvents containing the appropriate acid and isolating the salt by evaporating the solution. Examples of pharmaceutically acceptable salts are hydrochlorides, hydrobromides, hydrosulfates, etc. as well as sodium, potassium, and magnesium, etc. salts.

The compounds of Formula II can contain one or several asymmetric carbon atoms. The invention includes the individual diastereomers or enantiomers, and the mixtures thereof. The individual diastereomers or enantiomers may be prepared or isolated by methods already well-known in the art.

The term "caffeine" as used herein is intended to encompass not only caffeine as the anhydrous powder, but any salt or derivative of caffeine or any compounded mixture thereof which is non-toxic, pharmaceutically acceptable and which is capable of hastening and enhancing an analgesic or anti-inflammatory response when employed as described herein. See, for example, The Merck Index, ninth edition, Merck & Co., Inc. Rahway, N.J. (1976), pp. 207–208, for a description of caffeine salts, derivatives and mixtures that may prove useful in the compositions of the present invention. Nevertheless, caffeine as the anhydrous powder base is presently preferred and, where specific amounts of caffeine are set forth below, such amounts are given in mg of the anhydrous base.

The amount of caffeine in the composition will be an amount sufficient to further enhance analgesia or to hasten its onset. In humans, this amount will typically be from about 60 to about 200 mg (preferably 65 to 150 mg), an amount generally sufficient to both hasten onset and enhance analgesia. The daily dosage of caffeine again will generally not exceed 1000 mg. Of course, greater amounts can be used if tolerated by the patient. An additional advantage in using caffeine in the compositions and methods of the present invention is to offset the drowsiness or sedation experienced by approximately one-fifth of the users of GABA analogs.

A unit dosage form of the GABA analog/caffeine-combination used in this invention may also comprise other compounds useful in the treatment of pain.

While the compositions of the invention are preferably for oral use, they may also be formulated for and administered by other methods that are known for administering analgesics, e.g. as suppositories. Also, the preferred human dosage levels indicated above are for use in adults; pediatric compositions would contain proportionately less of the active ingredients.

The compositions of the present invention are very conveniently administered to mammals by any route of administration suitable for the selected GABA analog, e.g. oral or rectal. Preferably, the combination is formulated with any suitable nontoxic pharmaceutically acceptable inert carrier material. Such carrier materials are well known to those skilled in the art of pharmaceutical formulations. For those not skilled in the art, reference is made to the text entitled, "REMINGTON'S PHARMACEUTICAL SCIENCES" (Fourteenth Edition), 1970.

In a typical preparation for oral administration, e.g., tablet or capsule, the selected GABA analog in an effective amount and caffeine in an amount sufficient to enhance the effect of the GABA analog or to hasten its onset, are combined with any oral nontoxic pharmaceutically acceptable inert carrier such as lactose, starch (pharmaceutical grade), dicalcium phosphate, calcium sulfate, kaolin, mannitol and powdered sugar.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Additionally, when required, suitable binders, lubricants, disintegrating agents and coloring agents can also be included. Typical binders include starch, gelatin, sugars such as sucrose, molasses and lactose, natural and synthetic gums such as acacia, sodium alignate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citris pulp, carboxymethylcellulose and sodium lauryl sulfate. If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. Such compositions should preferably contain at least 0.1% of active components; generally, the active ingredients will be between about 2% to about 60% of the weight of the dosage unit. The compositions can, if desired, also contain other therapeutic agents.

The percentage of the active ingredients in the foregoing compositions can be varied within wide limits, but for practical purposes it is preferably present in a concentration of at least 10% in a solid composition and at least 2% in a primary liquid composition. The most satisfactory compositions are those in which a much higher proportion of the active ingredient is present.

The advantages of using the compounds of Formula I and II, especially gabapentin and pregabalin, in the instant invention include the relatively nontoxic nature of the compounds, the ease of preparation, the fact that the compounds are well-tolerated, and the ease of IV administration of the drugs. Gabapentin has few interactions with major classes of drugs since it is not metabolized in the liver, but rather excreted unchanged from the body. Further, the drugs are not metabolized in the body. The subjects treated with the method of the present invention are mammals, including humans.

We claim:

1. A method for eliciting an enhanced analgesic response in a mammal, comprising administering to said mammal a pharmaceutical composition comprising:

(a) an analgesically effective amount of a GABA analog; and (b) an effective amount of caffeine.

2. The method according to claim 1, wherein the GABA analog is the compound according to Formula I:

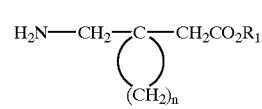

wherein $R_1$ is hydrogen or lower alkyl and n is an integer of from 4 to 6, and the pharmaceutically acceptable salts thereof.

3. The method according to claim 2, wherein Formula I comprises gabapentin.

4. The method according to claim 1, comprising from about 60 mg to about 200 mg caffeine.

5. The method according to claim 4, comprising from about 65 mg to about 150 mg caffeine.

6. The method according to claim 2, comprising from about 10 mg to about 400 mg of Formula I.

7. The method according to claim 3, comprising from about 10 mg to about 400 mg of gabapentin.

8. The method according to claim 1, comprising from about 10 mg to about 400 mg of GABA analog and from about 60 mg to about 200 mg caffeine.

9. The method according to claim 2, comprising from about 10 mg to about 400 mg of the compound according to Formula I and from about 60 mg to about 200 mg caffeine.

10. The method according to claim 3, comprising from about 10 mg to about 400 mg of gabapentin and from about 60 mg to about 200 mg caffeine.

11. The method according to claim 1, wherein the GABA analog is a compound according to Formula II:

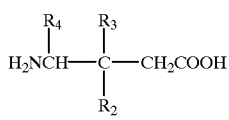

wherein $R_2$ is a straight or branched alkyl of from 1 to 6 carbon atoms, phenyl, or cycloalkyl having from 3 to 6 carbon atoms; $R_3$ is hydrogen or methyl; and $R_4$ is hydrogen, methyl, or carboxyl.

12. The method according to claim 11, wherein Formula II comprises pregabalin.

13. The method according to claim 11, comprising from about 60 mg to about 200 mg caffeine.

14. The method according to claim 13, comprising from about 65 mg to about 150 mg caffeine.

15. The method according to claim 11, comprising from about 0.15 mg to about 65 mg of Formula II.

16. The method according to claim 12, comprising from about 0.15 mg to about 0.15 mg of pregabalin.

17. The method according to claim 11, comprising from about 0.15 mg to about 65 mg compound according to Formula II and from about 60 mg to about 200 mg caffeine.

18. The method according to claim 12, comprising from about 0.15 mg to about 65 mg of gabapentin and from about 60 mg to about 200 mg caffeine.

19. A composition for eliciting an enhanced analgesic response in a mammal comprising:
(a) an analgesically effective amount of a GABA analog wherein the GABA analog is a compound according to Formula II:

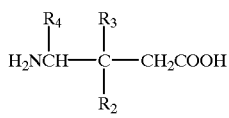

wherein $R_2$ is a straight or branched alkyl of from 1 to 6 carbon atoms, phenyl or phenyl, or cycloalkyl having from 3 to 6 carbon atoms; $R_3$ is hydrogen or methyl; and $R_4$ is hydrogen, methyl, or carboxyl; and
(b) an effective amount of caffeine.

20. The composition according to claim 19, wherein Formula II comprises pregabalin.

21. The composition according to claim 19, comprising from about 60 mg to about 200 mg caffeine.

22. The composition according to claim 21, comprising from about 65 mg to about 150 mg caffeine.

23. The composition according to claim 19 comprising from about 0.15 mg to about 65 mg of Formula II.

24. The composition according to claim 20, comprising from about 0.14 mg to about 65 mg of pregabalin.

25. The composition according to claim 19, comprising from about 0.15 mg to about 65 mg of the compound according to Formula II and from about 60 mg to about 200 mg caffeine.

26. The composition according to claim 20, comprising from about 0.15 mg to about 65 mg of pregabalin and from about 60 mg to about 200 mg caffeine.

27. A method for eliciting an enhanced analgesic response in a mammal, comprising administering to said mammal a pharmaceutical composition comprising:

(a) an analgesically effective amount of a GABA analog wherein the GABA analog is a compound according to Formula I:

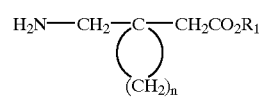

wherein $R_1$ is hydrogen or lower alkyl and n is an integer of from 4 to 6, and the pharmaceutically acceptable salts thereof or Formula II:

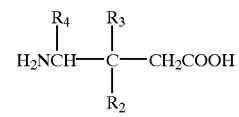

wherein $R_2$ is a straight or branched alkyl of 1 to 6 carbon atoms, phenyl, cycloalkyl having from 3 to 6 carbon atoms; $R_3$ is hydrogen of methyl; and $R_4$ is hydrogen, methyl, or carboxyl; and
(b) an effective amount of caffeine.

28. The method according to claim 27, wherein Formula I comprises gabapentin.

29. The method according to claim 27, comprising from about 60 mg to about 200 mg caffeine.

30. The method according to claim 29, comprising from about 65 mg to about 150 mg caffine.

31. The method according to claim 27, comprising from about 10 mg to about 400 mg of Formula I.

32. The method according to claim 28, comprising from about 10 mg to about 400 mg of gabapentin.

33. The method according to claim 27, comprising from about 10 mg to about 400 mg of GABA analog and from about 60 mg to about 200 mg caffeine.

34. The method according to claim 37, comprising from about 10 mg to about 400 mg of the compound according to Formula I and from about 60 mg to about 200 mg caffeine.

35. The method according to claim 38, comprising from about 10 mg to about 400 mg of gabapentin and from about 60 mg to about 200 mg caffeine.

36. The method according to claim 27, wherein Formula II comprises pregabalin.

37. The method according to claim 27, comprising from about 60 mg to about 200 mg caffeine.

38. The method according to claim 37, comprising from about 65 mg to about 150 mg caffeine.

39. The method according to claim 27, comprising from about 0.15 mg to about 65 mg of Formula II.

40. The method according to claim 36, comprising from about 0.15 mg to about 0.15 mg of pregabalin.

41. The method according to claim 27, comprising from about 0.15 mg to about 65 mg compound according to Formula II and from about 60 mg to about 200 mg caffeine.

42. The method according to claim 36, comprising from about 0.15 mg to about 65 mg of gabapentin and from about 60 mg to about 200 mg caffeine.

* * * * *